United States Patent
Chatellier (10) Patent No.: US 9,683,969 B2
(45) Date of Patent: Jun. 20, 2017

(54) METHOD OF CHARACTERIZING AN OBJECT INCLUDING, AT LEAST LOCALLY, A PLANE OF SYMMETRY

(71) Applicant: SNECMA, Paris (FR)

(72) Inventor: Jean-Yves Francois Roger Chatellier, Arcueil (FR)

(73) Assignee: SNECMA, Paris (FR)

( * ) Notice: Subject to any disclaimer, the term of this patent is extended or adjusted under 35 U.S.C. 154(b) by 0 days.

(21) Appl. No.: 14/413,133

(22) PCT Filed: Jul. 2, 2013

(86) PCT No.: PCT/FR2013/051556
§ 371 (c)(1),
(2) Date: Jan. 6, 2015

(87) PCT Pub. No.: WO2014/009632
PCT Pub. Date: Jan. 16, 2014

(65) Prior Publication Data
US 2015/0198565 A1    Jul. 16, 2015

(30) Foreign Application Priority Data
Jul. 10, 2012 (FR) ...................... 12 56629

(51) Int. Cl.
*G01N 29/07* (2006.01)
*G01N 29/04* (2006.01)
(Continued)

(52) U.S. Cl.
CPC ............ *G01N 29/07* (2013.01); *G01M 13/00* (2013.01); *G01N 29/04* (2013.01); *G01N 29/221* (2013.01);
(Continued)

(58) Field of Classification Search
CPC ...... G01N 29/07; G01N 29/04; G01N 29/221; G01N 2291/023; G01N 2291/0289;
(Continued)

(56) References Cited

U.S. PATENT DOCUMENTS 4,289,032 A * 9/1981 Tominaga ............ A63B 47/008
                                                  473/351
4,387,596 A * 6/1983 Fenkner ................ G01N 29/27
                                                    73/593
(Continued)

FOREIGN PATENT DOCUMENTS

DE    199 57 905 A1    5/2001
WO    WO 2013009331 A1 *  6/2013

OTHER PUBLICATIONS

R. N. McCartney, et al., "Transverse path of ultrasound waves in thick-walled cylinders" Medical and Biological Engineering & Computing, vol. 33, No. 4, XP000516477, Jul. 1, 1995, pp. 551-557.

*Primary Examiner* — Laura Martin
*Assistant Examiner* — Rose M Miller
(74) *Attorney, Agent, or Firm* — Oblon, McClelland, Maier & Neustadt, L.L.P.

(57) ABSTRACT

A method of characterizing an object that includes, at least locally, a plane of symmetry, the method including performing at least one observation of ultrasound transmitted through the object, each observation being performed on an axis perpendicular to the plane of symmetry, each observation resulting from an emission of ultrasound generated along a respective one of the axes and meeting the object along the axis at an angle of incidence other than normal, the ultrasound meeting the object to follow a path that is symmetrical relative to the plane of symmetry.

10 Claims, 8 Drawing Sheets (51) Int. Cl.
*G01N 29/22* (2006.01)
*G01M 13/00* (2006.01)

(52) U.S. Cl.
CPC .. *G01N 2291/011* (2013.01); *G01N 2291/023* (2013.01); *G01N 2291/0289* (2013.01); *G01N 2291/048* (2013.01); *G01N 2291/0421* (2013.01); *G01N 2291/0422* (2013.01); *G01N 2291/0423* (2013.01); *G01N 2291/102* (2013.01); *G01N 2291/265* (2013.01); *G01N 2291/2696* (2013.01)

(58) Field of Classification Search
CPC ... G01N 2291/0421; G01N 2291/0422; G01N 2291/0423; G01N 2291/048; G01N 2291/102; G01N 2291/265; G01N 2291/2696
USPC ........................................................ 73/597
See application file for complete search history.

(56) References Cited

U.S. PATENT DOCUMENTS

| | | | |
|---|---|---|---|
| 4,543,817 A | * | 10/1985 | Sugiyama ............. G01M 3/243 73/40.5 A |
| 4,890,496 A | | 1/1990 | Birring et al. |
| 5,005,417 A | * | 4/1991 | Kawasaki ............. G01N 29/041 73/593 |
| 5,195,372 A | * | 3/1993 | Fushimi ................ G01N 29/11 73/593 |
| 5,243,862 A | | 9/1993 | Latimer |
| 5,257,544 A | * | 11/1993 | Khuri-Yakub ......... G01H 13/00 73/579 |
| 2009/0019937 A1 | | 1/2009 | Deemer et al. |

* cited by examiner

METHOD OF CHARACTERIZING AN OBJECT INCLUDING, AT LEAST LOCALLY, A PLANE OF SYMMETRY

TECHNICAL FIELD AND PRIOR ART

The invention lies in the field of methods of studying and characterizing parts in industry, in particular for determining their bulk mechanical properties and their surface characteristics.

The invention applies in particular to elements of small size for which it is not possible to carry out mechanical testing in traction. This applies for example to balls for ball bearings, which have a diameter of centimeter order. The invention is particularly for use with parts presenting a surface that is curved in a section plane.

At present, no solution is known for determining the internal isotropy of such a small element, or for determining its mechanical characteristics such as its Young's modulus or its Poisson's ratio. Nevertheless, it is important to have good knowledge about such parts in order to ensure that bearings are reliable.

Characterization techniques are known that make use of ultrasonic wave measurements, in particular using reflected waves, but also using refracted waves or surface waves.

Thus, documents FR 2 806 162 and EP 1 691 193 describe defect detection systems using a transducer for measuring reflected waves, in which the surface of the material irradiated by the ultrasound is plane.

Document EP 1 767 898 discloses using a Rayleigh wave, which is a surface wave, that is produced at the surface of a part exposed to an incident ultrasound wave, in order to measure the thickness of a surface layer, such as a layer of nitriding.

Document FR 2 930 034 teaches using the longitudinal reflected wave to measure residual stresses in a material that has been subjected to treatment.

For these various purposes, use is made of ultrasonic transducers for performing inspection by contact, or ultrasonic transducers for performing inspection on parts that are immersed. Methods using such transducers have the advantage of being nondestructive.

DEFINITION OF INVENTION—ADVANTAGES PROVIDED THEREBY

The proposed invention is a method of characterizing an object that includes, at least locally, a plane of symmetry, the method comprising at least one observation of ultrasound transmitted through said object, each observation being performed on an axis perpendicular to the plane of symmetry, each observation resulting from an emission of ultrasound meeting the object along said axis at an angle of incidence other than normal, the ultrasound meeting the object in such a manner as to follow a path that is symmetrical relative to the plane of symmetry.

Analysis of the travel time of the ultrasound wave and/or of the position of the axis on which the emission and the observation are performed makes it possible to characterize the object, regardless of whether it is small or large, thus constituting a major advantage compared with prior art techniques, which do not make it possible to characterize an element that is small.

The fact that the ultrasound meets the object at an angle of incidence that is other than the normal makes it possible to use the surface of the object as a mode-conversion tool (bulk waves or surface waves), thereby providing additional information compared with observing a wave that is transmitted or reflected.

The use of a path that is symmetrical relative to a plane of symmetry makes it possible to use facing emit and receive transducers that are easy to put into place and to adjust.

In a particular embodiment, the emit and receive ultrasound transducers positioned on a common axis are shifted while emitting ultrasound and observing transmitted ultrasound, and observations are made on at least two waves selected from the longitudinal, transverse, and Rayleigh waves created by the emitted ultrasound. The properties determined by such a characterization method may include the Young's modulus or the Poisson's ratio of the object.

It may be advantageous to observe all three waves from among the longitudinal, transverse, and Rayleigh waves, and to validate the method by using Viktorov's formula.

In another implementation, for an object having a second plane of symmetry perpendicular to the first plane of symmetry, the emit and receive ultrasound transducers positioned on a common axis are shifted on either side of the second plane of symmetry while emitting ultrasound and observing transmitted ultrasound, and two longitudinal waves or two transverse waves are observed on opposite sides of the second plane of symmetry. The properties of the object that are determined by such a characterization method may include whether it has an isotropic or an anisotropic character in at least one plane.

In another implementation, observations are made of at least one Rayleigh wave created at the surface of said object by the ultrasound meeting it. Measuring the travel time makes it possible to detect the presence of a layer or of a zone that results from applying surface treatment to the object.

The invention is particularly applicable when the object has a surface that includes at least one arc of an ellipse, or an arc of a circle. In particular, the object is a bearing ball or roller, but other applications are possible.

DETAILED DESCRIPTION OF EMBODIMENTS

Figure 1:
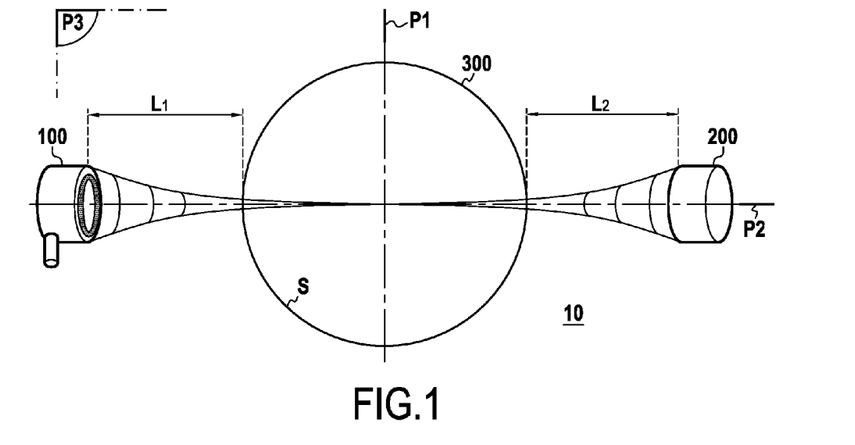
FIG. 1 shows a preliminary step in an implementation of a method of the invention.

FIG. 1 shows a step of adjusting characterization apparatus for characterizing a bearing ball. The apparatus is based on using immersed ultrasonic transducers.

The apparatus comprises a first ultrasonic transducer 100 and a second ultrasonic transducer 200, in a volume of water 10. They are positioned on a common axis, facing each other, on opposite sides of a bearing ball that constitutes a sphere 300. In this example, they are 4 inch focused transducers of the Harisonic I7-1012-R type, having a frequency of 10 megahertz (MHz), a diameter of 0.75 inches, and a focal spot at the focus that is estimated as being 0.808 millimeters (mm). Other transducers could be used.

During the adjustment step, the transducers are actuated in emit mode and in receive mode. They are normally adjusted on the point of the sphere. Thus, in transmission mode, the two transducers 100 and 200 are accurately in alignment. The ultrasound beams generated in the water 10 are on the same axis.

The set-up constituted by the sphere and the two transducers has a plane of symmetry P1. The section of the sphere perpendicular to the plane P1 and in the plane containing the axis of the transducers presents a surface S that is a circle.

The travel time is measured corresponding to a go-and-return trip of the surface wave of the transducer focused on the point of the sphere being associated with the amplitude maximum in the received wave. The height of the column of water L1 between the transducer 100 and the surface of the sphere 300 is obtained by relating the time t1 read from the screen of the oscilloscope with the speed of the wave in water, i.e. $V_{water}$=1486.5 meters per second (m/s). The height of the column of water L2 between the transducer 200 and the surface of the sphere 300 is obtained in the same way.

Figure 2:
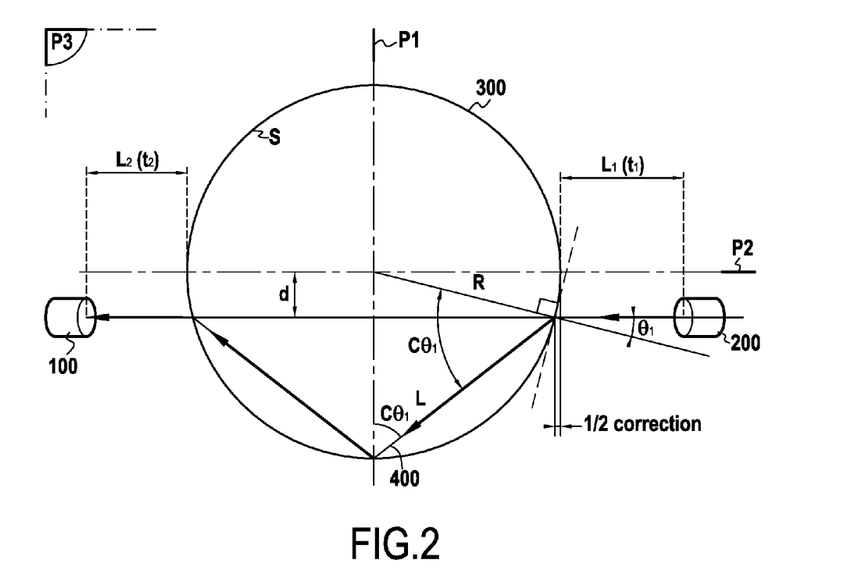
FIG. 2 shows a subsequent step in an implementation of a method of the invention.

FIG. 2 shows an elementary step of a method of the invention. Both transducers 100 and 200 have been translated by the same amount in a direction perpendicular to their common axis, starting from the configuration shown in FIG. 1, or from some other configuration.

Thereafter, signals are measured as received by one of the transducers, operating in receive mode (in this example the transducer 100), with the other transducer (the transducer 200) operating in emit mode.

For a given translation of the transducers, through a distance d relative to the initial position, the path of the ultrasound through the water is lengthened by an amount that is expressed as follows:

$$\text{correction} = 2.R(1 - \cos\theta_1)$$

The measured signals are stored and it can be seen, firstly by observing two maximums, that two transmitted waves are present, appearing at two distances d from the initial axis of the transducers.

The path of a wave is shown in FIG. 2, where it is given the reference 400. Going from the emitting transducer 200, the wave reaches the surface of the sphere 300 at an angle $\theta_1$ relative to the normal. It is deflected at the water/sphere interface by the phenomenon of refraction and it progresses through the sphere at an angle $C\theta_1$ relative to the normal. It reaches the surface of the sphere after traveling a distance L, and for the fraction of interest, it is reflected by that surface. Thereafter it follows a second path through the sphere, and reaches the surface once again, where it is refracted. Thereafter the wave propagates through the water.

The special feature of distances d for which maximums are observed is that reflection takes place at equal distances from both transducers, and that the wave, after being refracted twice, propagates towards the receive transducer 100.

Furthermore, by taking advantage of the fact that reflection takes place with an angle $2 \times C\theta_1$, which is due to the symmetrical nature of the ball, the following applies:

$$\tan C\theta_1 = \frac{(R - \text{correction}/2)}{(R - d)}$$

Snell's law then makes it possible to obtain the angle $C\theta_1$, which is given as follows:

$$C\theta_1 = \tan^{-1}\frac{R - d}{R\cos\theta_1}$$

The distance L traveled by the wave between one of the refractions (on entry or on exit) and the reflection is given as follows:

$$L = \frac{R - d}{\sin C\theta_1}$$

The travel time of the wave inside the sphere 300 can be deduced by taking account of the correction associated with the lengthening of the columns of water L1 and L2. The speed of propagation of the wave in the sphere can be deduced therefrom.

This calculation is performed for the longitudinal wave, which is the first to appear when the transducers are shifted from their initial positions, and then for the transverse wave, which appears subsequently with greater amplitude.

By continuing to shift the transducers, a third wave is observed, which is a surface wave, known as the Rayleigh wave. This wave appears only for a particular angle of incidence. Once it has been created, it radiates while it is propagating along the surface, with an angle that is equal to the angle of the incident wave that created it, specifically in this example, the angle $\theta_1$.

By writing the diameter of the sphere as $\varphi$, the distance traveled by the Rayleigh wave that is picked up by the receive transducer is the length of a sector of a circle that is expressed as follows:

$$L = \frac{2\pi\varphi}{4}\left(\frac{90 - \theta_1}{90}\right).$$

Knowing this distance and also the corrected length for the water columns, it is easy to determine the propagation speed of the Rayleigh wave.

Figure 3:
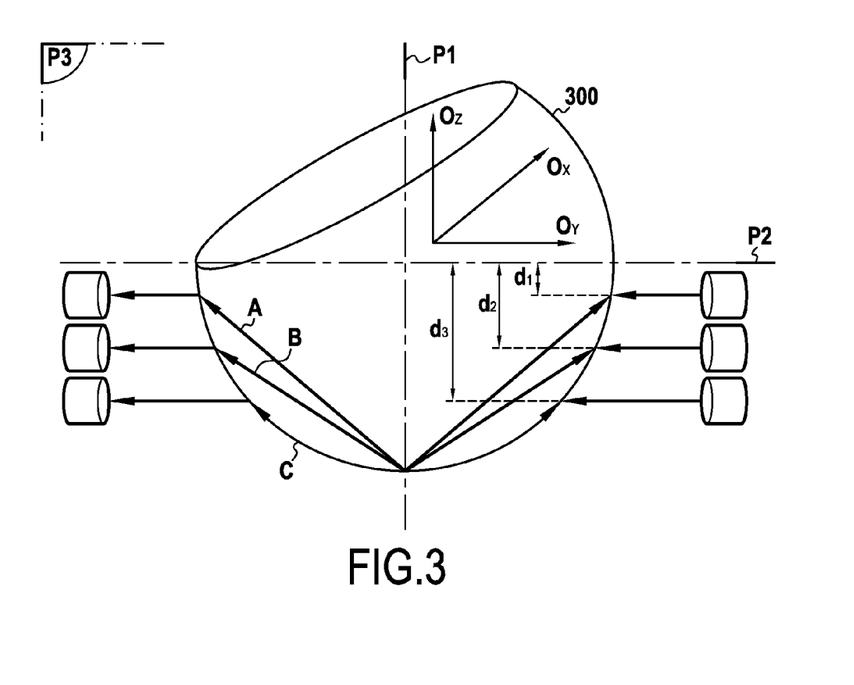
FIG. 3 shows the important elements in an implementation of the invention.

FIG. 3 shows the three waves detected in succession during shifting of the transducers: the longitudinal wave A, the transverse wave B, and the Rayleigh wave C.

Using the speeds of the waves, Poisson's ratio and Young's modulus for the material of the sphere 300 can be deduced.

This method has been applied to a bearing ball made of stainless steel having a radius of 9.523 mm. The results obtained were as follows.

Longitudinal Wave
  d=1.729 mm
  $\theta_1$=10.46°
  Travel time in water=132.64 microseconds (µs)
  $C\theta_1$=39.77°
  L=12.183 mm
  Measured travel time=136.73 µs
  Speed in the sphere=5957.4 m/s
Transverse Wave
  d=3.539 mm
  $\theta_1$=21.82°
  Travel time in water=133.35 µs
  $C\theta_1$=34.09°
  L=21.351 mm
  Measured travel time=139.94 µs
  Speed in the sphere=3238.8 m/s Rayleigh Wave
 d=4.677 mm
 $\theta_1$=29,415°
 Travel time in water=131,106 µs
 L=20.139 mm
 Measured travel time=137.80 µs
 Speed at the surface of the sphere=3008.9 m/s The method can be validated by comparing the speed deduced for the Rayleigh wave by measurement with the speed obtained by Viktorov's law on the basis of the speeds of the longitudinal and transverse waves, using the following formula:

$$V_R = V_T \frac{0.718 - \frac{V_T^2}{V_L^2}}{0.75 - \frac{V_L^2}{V_L^2}}.$$

The speed of the Rayleigh wave obtained by Viktorov's law is 3010.7 m/s, which is very close to the value obtained by measurement.

The values of at least two of the waves selected from the transverse wave, the longitudinal wave, and the Rayleigh wave are then used to deduce Young's modulus and Poisson's ratio for the material of the sphere, which is assumed to be homogeneous.

The following values are obtained:
 Young's modulus E=211.7 giga pascals (GPa)
 Poisson's ratio=0.290.

Figure 4:
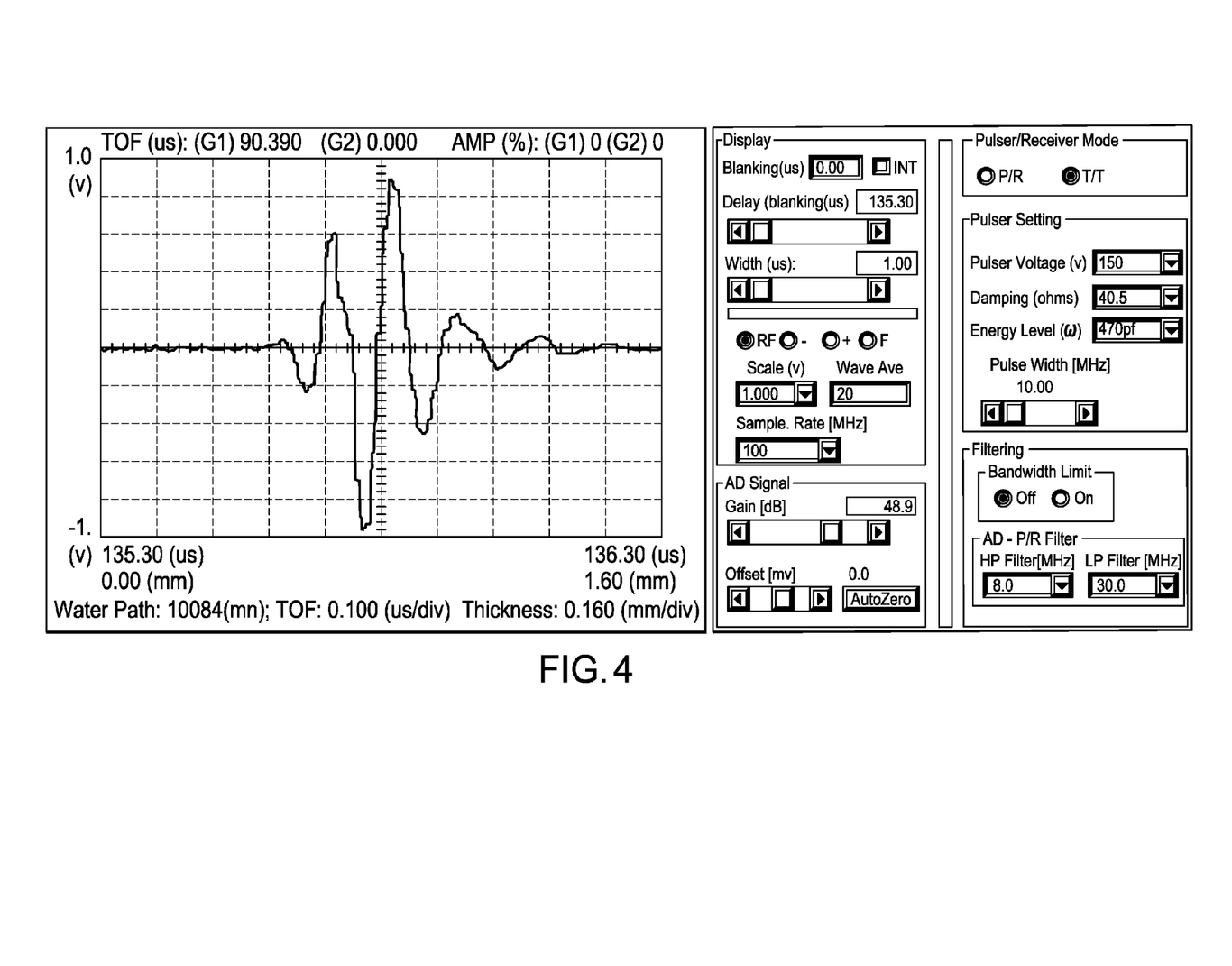
FIGS. 4 to 9 show displays of important elements shown in FIG. 3, for two utilizations of the method of the invention.
Figure 5:
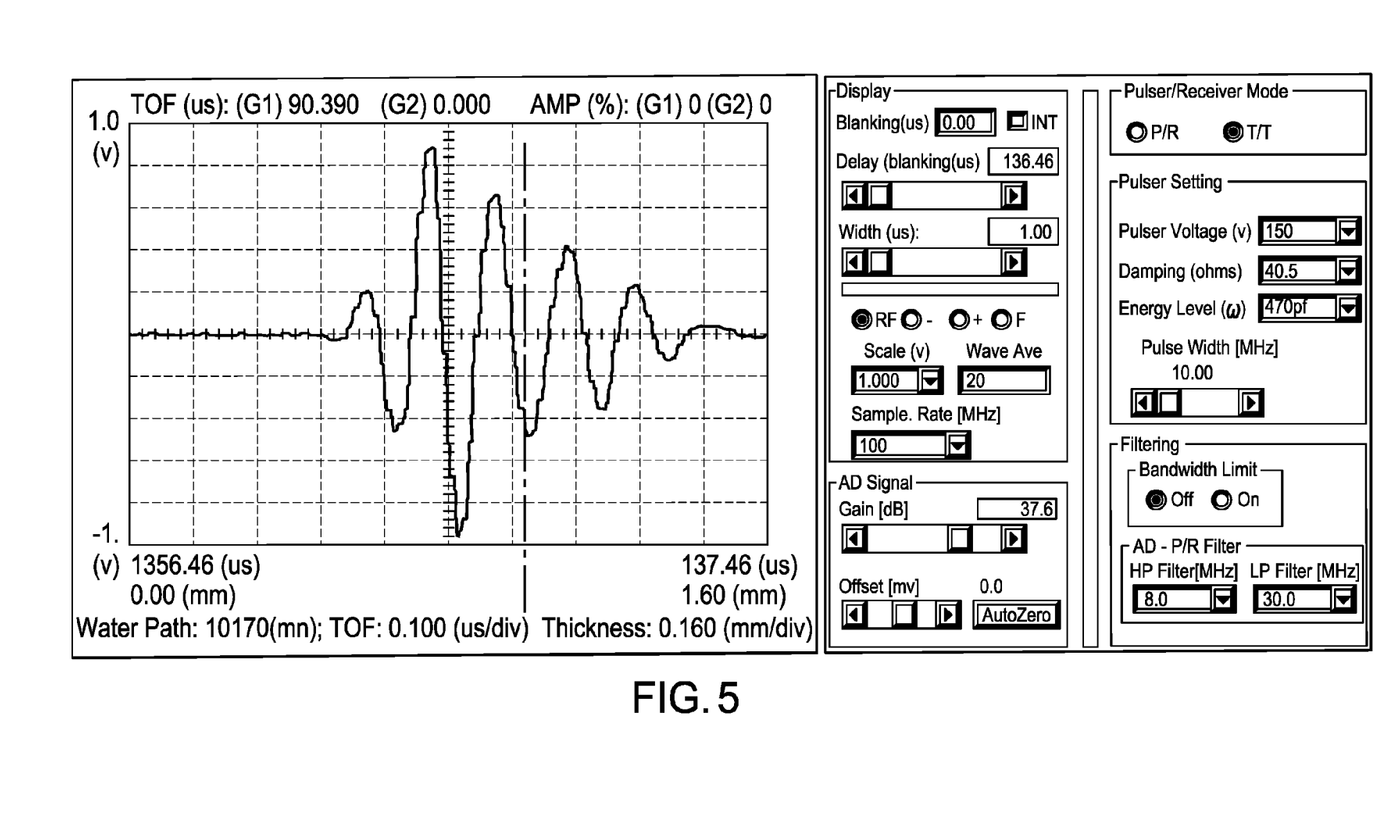
Figure 6:
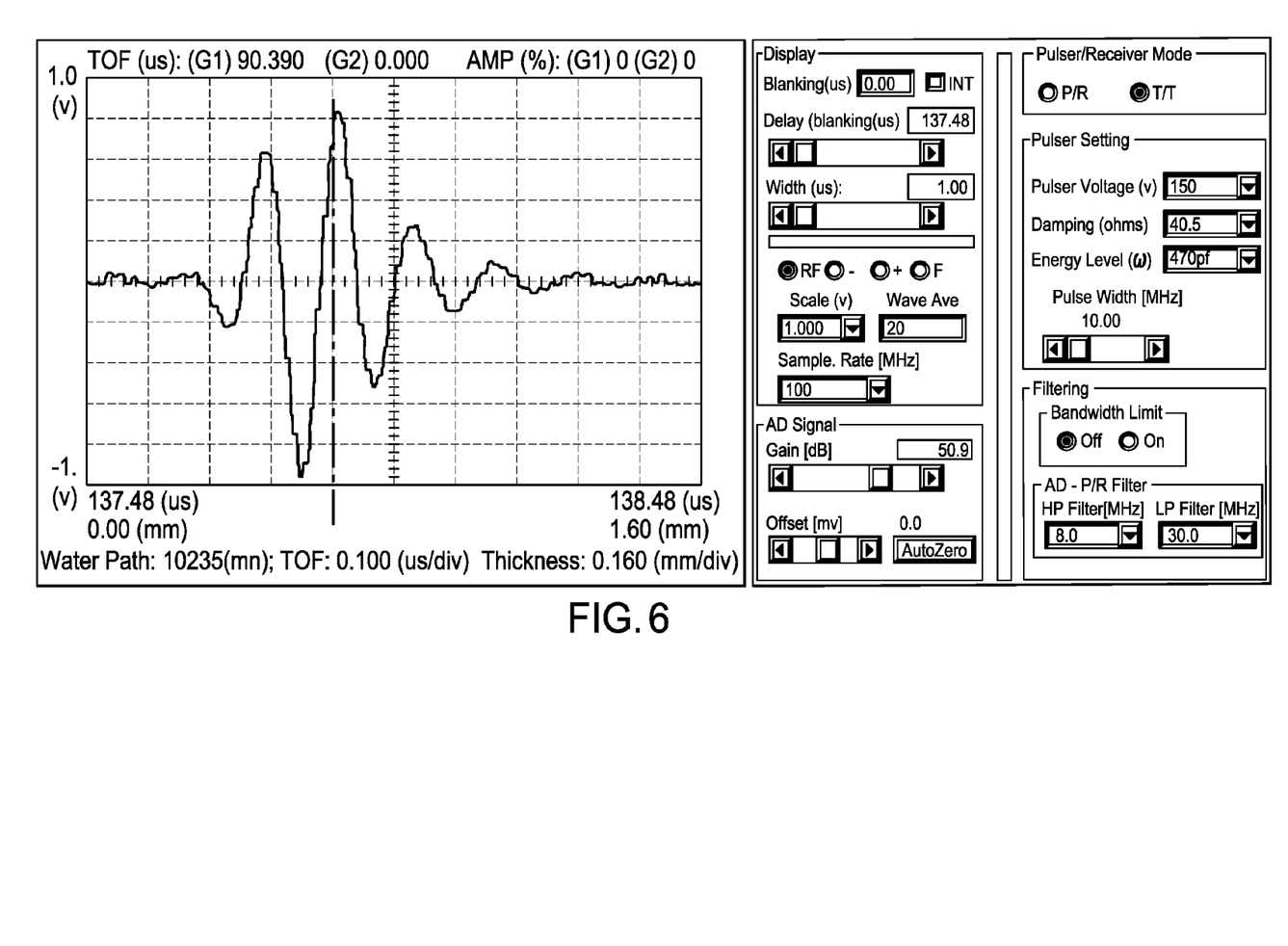

FIGS. 4 to 6 show the spectra observed by the receive transducer 100. In FIG. 4, an amplitude maximum can be observed at d=1.729 mm for the longitudinal wave. In FIG. 5, an amplitude maximum can be observed at d=3.539 mm for the transverse wave, and in FIG. 6, an amplitude maximum can be observed at d=4.677 mm for the Rayleigh wave. It can be seen that it is the transverse wave that is transmitted with the greatest amplitude, whereas the Rayleigh wave is the most weakly transmitted of the three waves.

The method has also been applied to a ball of silicon nitride ($Si_3N_4$) having a radius of 4.7615 mm. The results obtained were as follows.
Longitudinal Wave
 V=11,827.3 m/s
Transverse Wave
 V=6377.9 m/s
Rayleigh Wave
 V=5916.6 m/s Viktorov's law gives 5933.4 m/s, which once more validates the method.

The mechanical characteristics of the ball as obtained on this basis are as follows:
 Young's modulus E=333.6 GPa
 Poisson's ratio=0.295.

Figure 7:
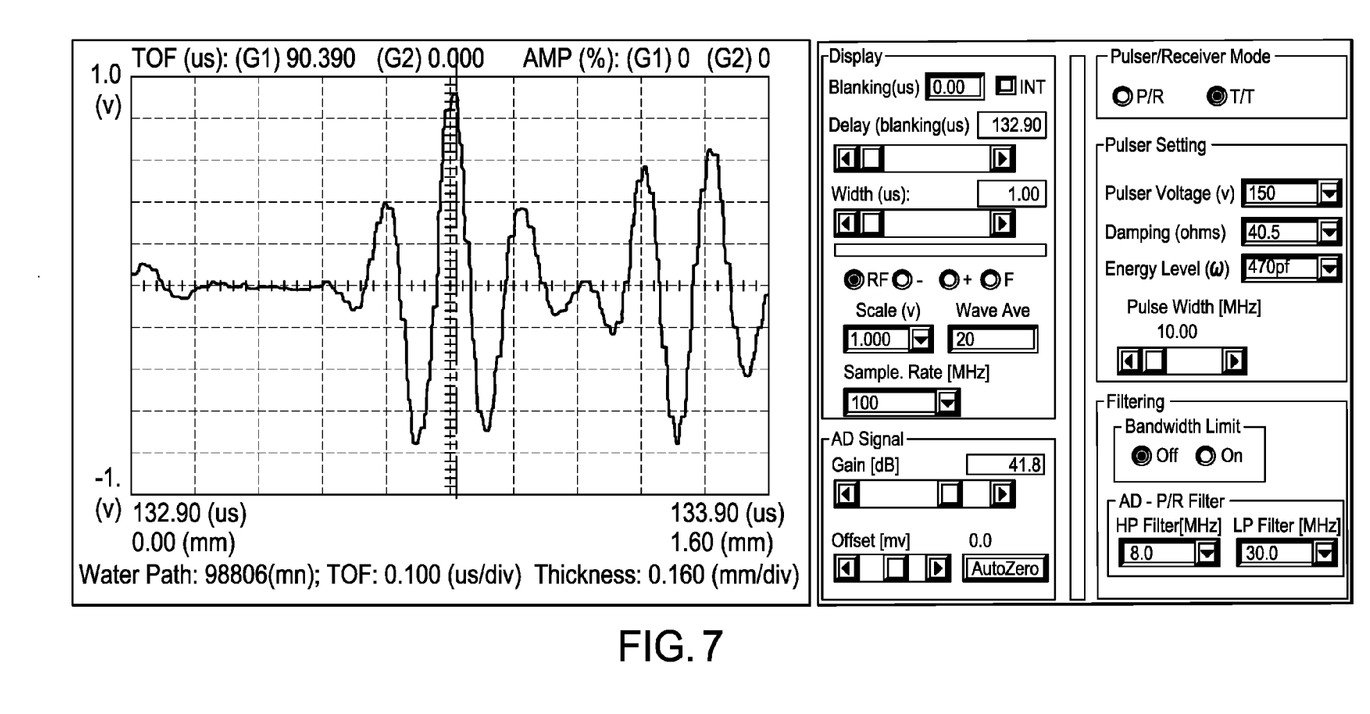
Figure 8:
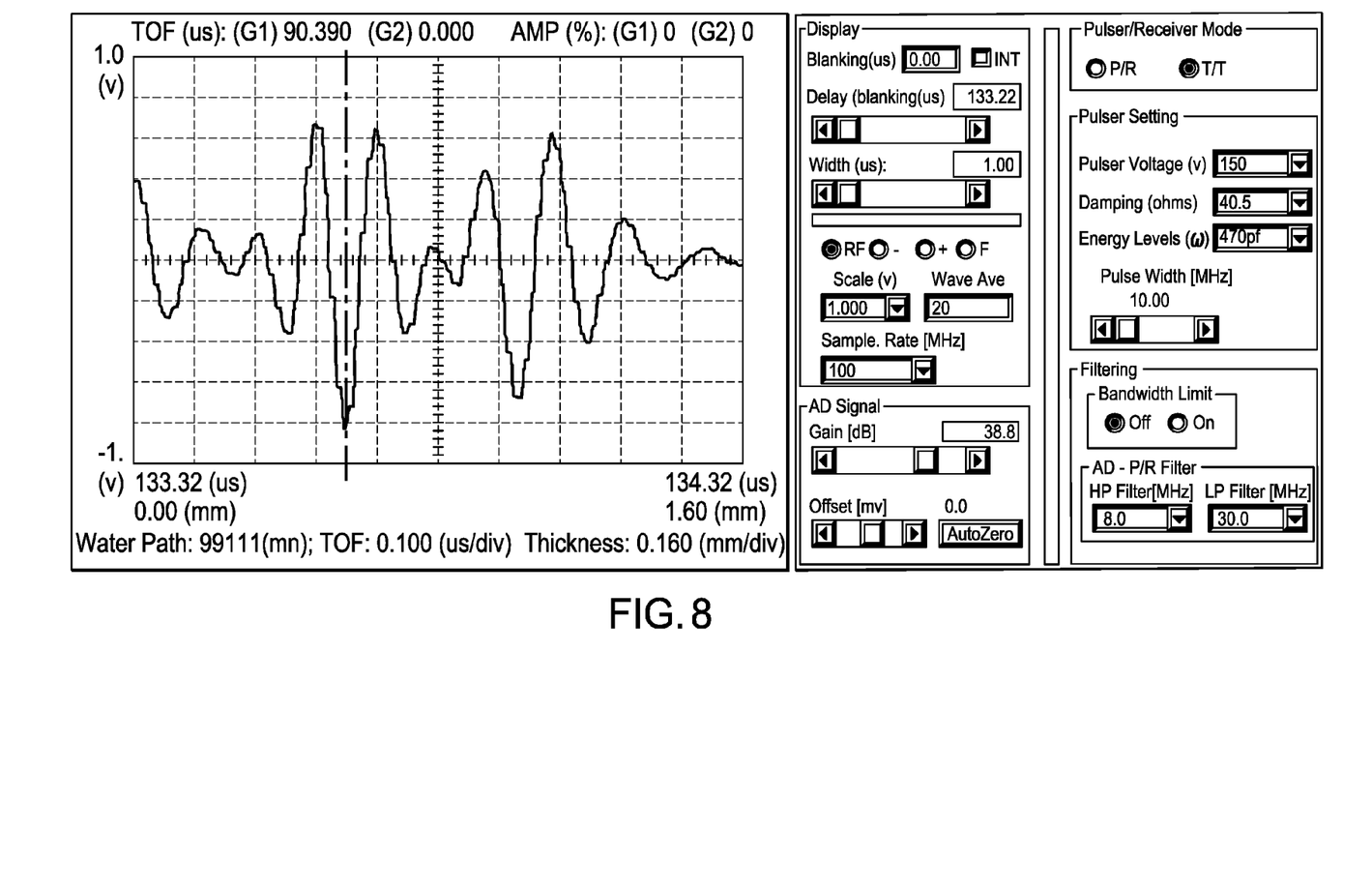
Figure 9:
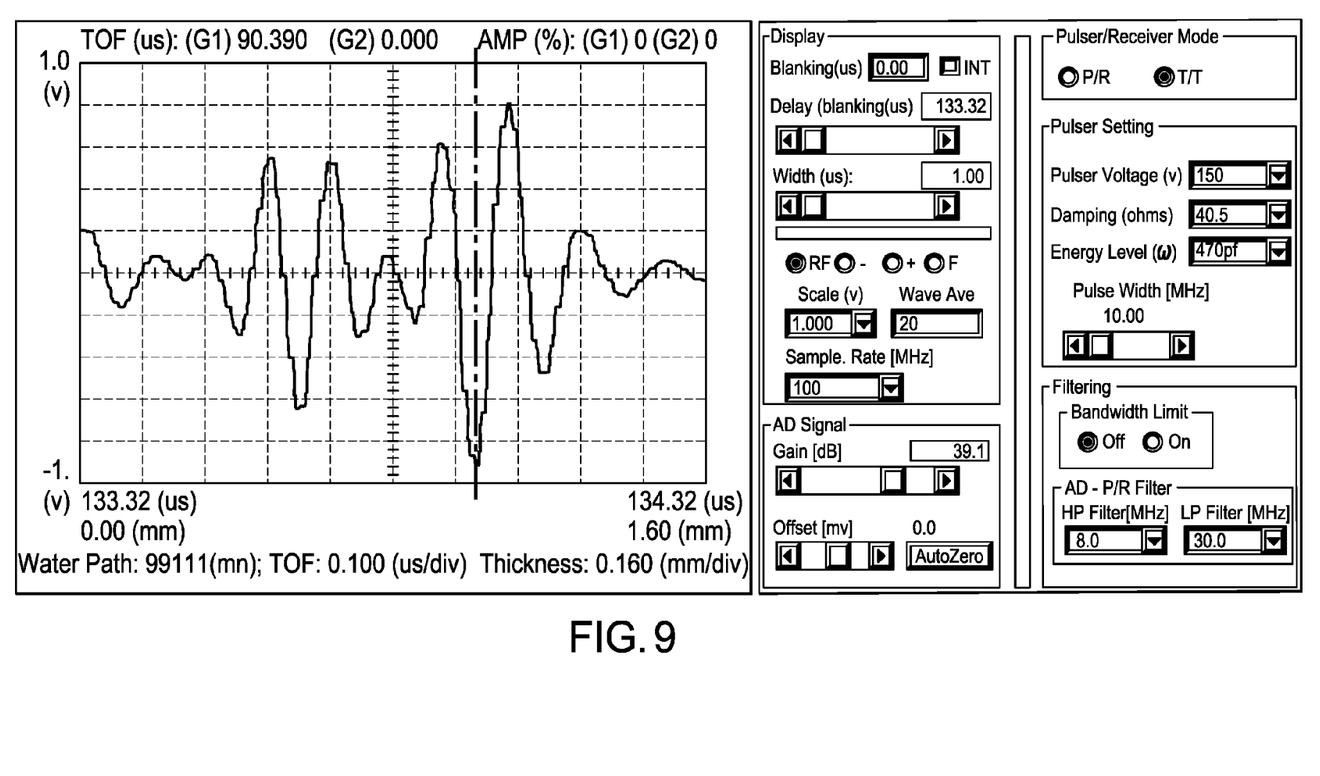

FIGS. 7 to 9 show the spectra observed by the receive transducer 100. The ordinate axis shows the measured voltage, and the abscissa axis shows time. In FIG. 7, an amplitude maximum can be observed at d=0.359 mm for the longitudinal wave. In FIG. 8, an amplitude maximum can be observed at d=0.753 mm for the transverse wave, and in FIG. 9, an amplitude maximum can be observed at d=1.007 mm for the Rayleigh wave.

Figure 10:
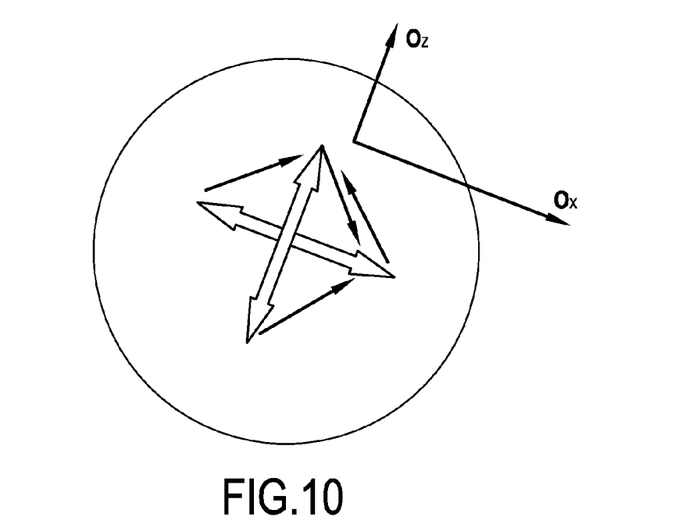
FIG. 10 shows the important elements in another implementation of the invention.

FIG. 10 shows a second implementation of the invention. The transducers are moved, still in parallel with each other, but this time along two orientations, in one direction and then in the opposite direction, starting from the initial alignment. Thus, the material of the ball is scanned in four directions. Use is made in particular of the fact that the sphere has a second plane of symmetry, written P2 (see FIGS. 1 to 3), together with a third plane of symmetry P3 (not shown), namely the plane of the figures. These two planes contain the initial alignment axis of the transducers.

If all four measurements give identical travel times for the shifts of the transducers at which any given wave, transverse or longitudinal, appears, then it can be concluded that the material of the ball is isotropic.

For the above-mentioned ball that is made of stainless steel, the following values were obtained for the transverse wave: Oz=−3.540 mm (t=139.94 µs), Oz=+3.540 mm (t=139.96 µs), Ox=−3.537 mm (t=139.96 µs) and Ox=+3.541 mm (t=139.94 µs).

Given the closeness of the values, it can be concluded that the ball is indeed isotropic.

For the ball made of silicon nitride, the following values were obtained, still for the transverse wave: Oz=−1.010 mm (t=133.94 µs), Oz=+1.125 mm (t=134.03 µs), Ox=−1.001 mm (t=133.99 µs) and Ox=+1.200 mm (t=133.99 µs).

Once more, given the closeness of the values, it can be concluded that the ball is indeed isotropic.

The isotropic or anisotropic nature of the ball may be studied by comparing the values obtained for the longitudinal waves. It is also possible to make do with measuring two values along one axis, e.g. Oz in the positive direction and Oz in the negative direction, giving information about isotropy in one plane.

In a third implementation, the Rayleigh wave, referenced C in FIG. 3, can be observed with a set up like that of FIG. 3. Measuring the position of the observation axis and/or determining the travel time of the wave on the surface make it possible to determine whether the sphere 300 has been subjected to a surface treatment, e.g. surface treatment such as nitriding, that changes the propagation speed of the Rayleigh wave because of the presence on the surface of a layer or a zone that is of a chemical nature or that has physical properties that are different from the initial material.

In a variant, one or more of the three waves shown in FIG. 3 are observed for a given example of the object 300, and the values for the distance d and/or for the travel time are compared with those obtained for a reference example of the object 300, so as to verify that the example under study matches the reference example.

The invention also applies to a roller cylinder, having a section that is circular, for example. The invention also applies to bearing balls or rollers of section that is elliptical, and more generally, to objects that are preferably convex and that have a plane of symmetry, and for example a surface that is curved in a plane perpendicular to the plane of symmetry. The assembly constituted by the two transducers is moved parallel to the plane of symmetry so as to direct the ultrasound onto the surface at different angles of incidence. When the transmitted wave is reflected in the plane of symmetry, it is picked up by the received transducer, and the travel time and/or the distance d make it possible to characterize the object. The plane of symmetry may be a plane of symmetry that is local, and the symmetry may apply to certain portions only of the object that is to be characterized.

The invention is not limited to the implementations described above, but extends to any variants in the context of the scope of the claims.

The invention claimed is:

1. A method of characterizing an object that includes, at least locally, a plane of symmetry, the method comprising:

performing at least one observation of an ultrasound wave transmitted through the object by a first ultrasound transducer and received by a second ultrasound transducer, each observation being performed on an observation axis perpendicular to the plane of symmetry, each observation including:

emitting of the ultrasound wave generated by the first ultrasound transducer along a transducer axis of the first ultrasound transducer and meeting the object along the transducer axis of the first ultrasound transducer at an angle of incidence other than normal, the ultrasound wave meeting the object to follow a path to the second ultrasound transducer that is symmetrical relative to the plane of symmetry, and     receiving the emitted ultrasound wave following the path by the second ultrasound transducer;

determining a travel time of the emitted ultrasound wave, and/or a position of the transducer axis and a position the observation axis; and     characterizing the object based on the travel time of the emitted ultrasound wave and/or the position of the transducer axis and the position of the observation axis.

2. A method according to claim 1, wherein the first and second ultrasound transducers positioned on a common axis are shifted while emitting the ultrasound wave and observing the emitted ultrasound wave, at least two waves selected from a longitudinal wave, a transverse wave, and a Rayleigh wave are transmitted and received, and observations are made on at least two waves selected from the longitudinal, transverse, and Rayleigh waves.

3. A method according to claim 2, wherein observations are made on all of three waves from the longitudinal, transverse, and Rayleigh waves, and the method further comprises determining speeds of the longitudinal, transverse, and Rayleigh waves, and validating the determined speed of the Rayleigh wave based on the speeds of the longitudinal and transverse waves.

4. A method according to claim 2, wherein the characterizing of the object includes determining Poisson's ratio and Young's modulus of the object.

5. A method according to claim 1, wherein, for the object having a second plane of symmetry perpendicular to the plane of symmetry, the first and second ultrasound transducers positioned on a common axis are shifted on either side of the second plane of symmetry while emitting the ultrasound wave and observing the transmitted ultrasound wave, and two longitudinal waves or two transverse waves are observed on opposite sides of the second plane of symmetry.

6. A method according to claim 1, wherein the at least one observation is made of at least one Rayleigh wave created at a surface of the object by the ultrasound wave meeting the object.

7. A method according to claim 1, wherein the first and second ultrasound transducers are immersion ultrasound transducers.

8. A method according to claim 1, wherein the object has a surface that includes at least one arc of an ellipse.

9. A method according to claim 8, wherein the surface includes at least one arc of a circle.

10. A method according to claim 1, wherein the object is a bearing ball or roller.

\* \* \* \* \*